United States Patent
Alpert et al.

(10) Patent No.: US 12,004,891 B1
(45) Date of Patent: Jun. 11, 2024

(54) METHODS AND SYSTEMS FOR DETECTION OF ERRORS IN MEDICAL REPORTS

(71) Applicant: Amazon Technologies, Inc., Seattle, WA (US)

(72) Inventors: Sharon Alpert, Rehovot (IL); Antonio Criminisi, Cambridge (GB)

(73) Assignee: Amazon Technologies, Inc., Seattle, WA (US)

( * ) Notice: Subject to any disclaimer, the term of this patent is extended or adjusted under 35 U.S.C. 154(b) by 503 days.

(21) Appl. No.: 17/217,675

(22) Filed: Mar. 30, 2021

(51) Int. Cl.
| | | |
|---|---|---|
| *A61B 6/00* | (2006.01) | |
| *A61B 5/055* | (2006.01) | |
| *A61B 6/03* | (2006.01) | |
| *A61B 8/08* | (2006.01) | |
| *G06F 3/0482* | (2013.01) | |

(Continued)

(52) U.S. Cl.
CPC ............ *A61B 6/5211* (2013.01); *A61B 5/055* (2013.01); *A61B 6/032* (2013.01); *A61B 8/5215* (2013.01); *G06F 3/0482* (2013.01); *G06F 3/1423* (2013.01); *G06F 18/22* (2023.01); *G06T 7/0012* (2013.01); *G06T 7/70* (2017.01); *G16H 15/00* (2018.01); *G16H 30/20* (2018.01); *G16H 30/40* (2018.01); *G16H 50/70* (2018.01); *G06T 2200/24* (2013.01); *G06T 2207/30004* (2013.01); *G06V 2201/031* (2022.01); *G10L 15/18* (2013.01); *G10L 15/22* (2013.01); *G10L 2015/223* (2013.01); *G16H 40/20* (2018.01); *G16H 50/20* (2018.01); *G16H 70/20* (2018.01); *G16H 70/60* (2018.01)

(58) Field of Classification Search
CPC ....... A61B 6/5211; A61B 5/055; A61B 6/032; A61B 8/5215; G06F 3/0482; G06F 3/1423; G06F 18/22; G06T 7/0012; G06T 7/70; G06T 2200/24; G06T 2207/30004; G16H 15/00; G16H 30/20; G16H 30/40; G16H 50/70; G16H 40/20; G16H 50/20; G16H 70/20; G16H 70/60; G06V 2201/031; G10L 15/18; G10L 15/22; G10L 2015/223
See application file for complete search history.

(56) References Cited

U.S. PATENT DOCUMENTS

| | | |
|---|---|---|
| 11,553,887 B2 | 1/2023 | McLaughlin |
| 2012/0316874 A1 | 12/2012 | Lipman |

(Continued)

OTHER PUBLICATIONS

U.S. Appl. No. 17/001,982, U.S. Patent Application, "Contextual Image Cropping and Report Generation," filed Aug. 25, 2020.

*Primary Examiner* — Tom Y Lu
(74) *Attorney, Agent, or Firm* — Kilpatrick Townsend & Stockton LLP

(57) ABSTRACT

Systems for preparing a medical report, and related methods, generate and output feedback indicative or potential errors in the medical report. A system for preparing a medical report is configured to receive image data for a medical image of a patient, display the medical image, monitor content of the medical report during preparation of the medical report, process the image data to detect one or more organs of the patient imaged in the medical image, compare the content of the medical report with the one or more organs imaged in the medical image to detect one or more potential errors in the medical report, and output feedback indicative of the one or more potential errors in the medical report.

20 Claims, 7 Drawing Sheets

(51) Int. Cl.
*G06F 3/14* (2006.01)
*G06F 18/22* (2023.01)
*G06T 7/00* (2017.01)
*G06T 7/70* (2017.01)
*G16H 15/00* (2018.01)
*G16H 30/20* (2018.01)
*G16H 30/40* (2018.01)
*G16H 50/70* (2018.01)
*G10L 15/18* (2013.01)
*G10L 15/22* (2006.01)
*G16H 40/20* (2018.01)
*G16H 50/20* (2018.01)
*G16H 70/20* (2018.01)
*G16H 70/60* (2018.01)

(56) References Cited

U.S. PATENT DOCUMENTS

| | | | |
|---|---|---|---|
| 2013/0326386 A1* | 12/2013 | Vendrell | G16H 50/30 715/771 |
| 2017/0154156 A1 | 6/2017 | Sevenster et al. | |
| 2018/0055468 A1 | 3/2018 | Reicher | |
| 2019/0138805 A1* | 5/2019 | Saha | G06V 30/413 |
| 2020/0126648 A1 | 4/2020 | Schadewaldt et al. | |
| 2020/0160982 A1 | 5/2020 | Gurson et al. | |
| 2020/0202523 A1 | 6/2020 | Ahn | |
| 2020/0357117 A1 | 11/2020 | Lyman et al. | |
| 2021/0074427 A1 | 3/2021 | Xu et al. | |
| 2021/0125706 A1 | 4/2021 | Spottiswoode et al. | |
| 2021/0166805 A1 | 6/2021 | Knoplioch | |
| 2021/0259664 A1 | 8/2021 | Hare, III et al. | |
| 2021/0313045 A1 | 10/2021 | Wu et al. | |
| 2021/0366106 A1 | 11/2021 | Yao et al. | |

* cited by examiner

METHODS AND SYSTEMS FOR DETECTION OF ERRORS IN MEDICAL REPORTS

BACKGROUND

Medical images are used extensively in disease diagnosis, treatment, monitoring, and drug discovery. Medical diagnostic reports typically include written descriptions of findings and results of medical tests and imaging. Medical diagnostic reports often describe and summarize important findings in medical images such as x-ray images, Computed Tomography (CT) images, Magnetic Resonance Imaging (MRI) images, ultrasound images and the like. Medical diagnostic reports often form a basis of resulting medical treatment.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Methods and systems described herein are directed to automated detection of potential errors and/or omissions in a medical image based medical report and providing feedback to a medical professional preparing the medical report to so as to reduce occurrence of errors and/or omissions in the medical report. In some embodiments, computer vision models that are trained to identify and localize organs in a medical image of a patient are used in conjunction with monitoring of the medical report during preparation of the medical report to detect organ identification errors and/or confirm organ identification. In some embodiments, the organs or portions of the patient identified in the medical image are used to limit what medical reports can be prepared based on the medical image to medical reports applicable to the identified organs or portions of the patient. In some embodiments, one or more computer vision models that are trained to detect and localize a pathology in a particular type of organ or portion of a patient are employed when the particular organ or portion is identified in the medical image of the patient so as to provide feedback configured to help avoid omissions in diagnosis. The feedback can be communicated using any suitable approach, such as via a suitable designation of reference to the organ or portion of the patient in the draft medical report and/or a suitable designation of an image of the organ or portion of the patient in the medical image of the patient. In many embodiments, the feedback is configured to alert the healthcare professional who is preparing the medical report to potential errors and/or omissions in the medical report to facilitate correction of the potential error and/or omission by the healthcare professional.

The system and techniques described herein can be used in connection with any suitable approach for preparing a medical image based medical report. For example, the systems and techniques described herein can be used in conjunction with preparation of the medical report via keyboard input and/or speech input. The keyboard input and/or speech input can be used to input both instructions regarding preparation of the medical report and content of the medical report.

Figure 1:
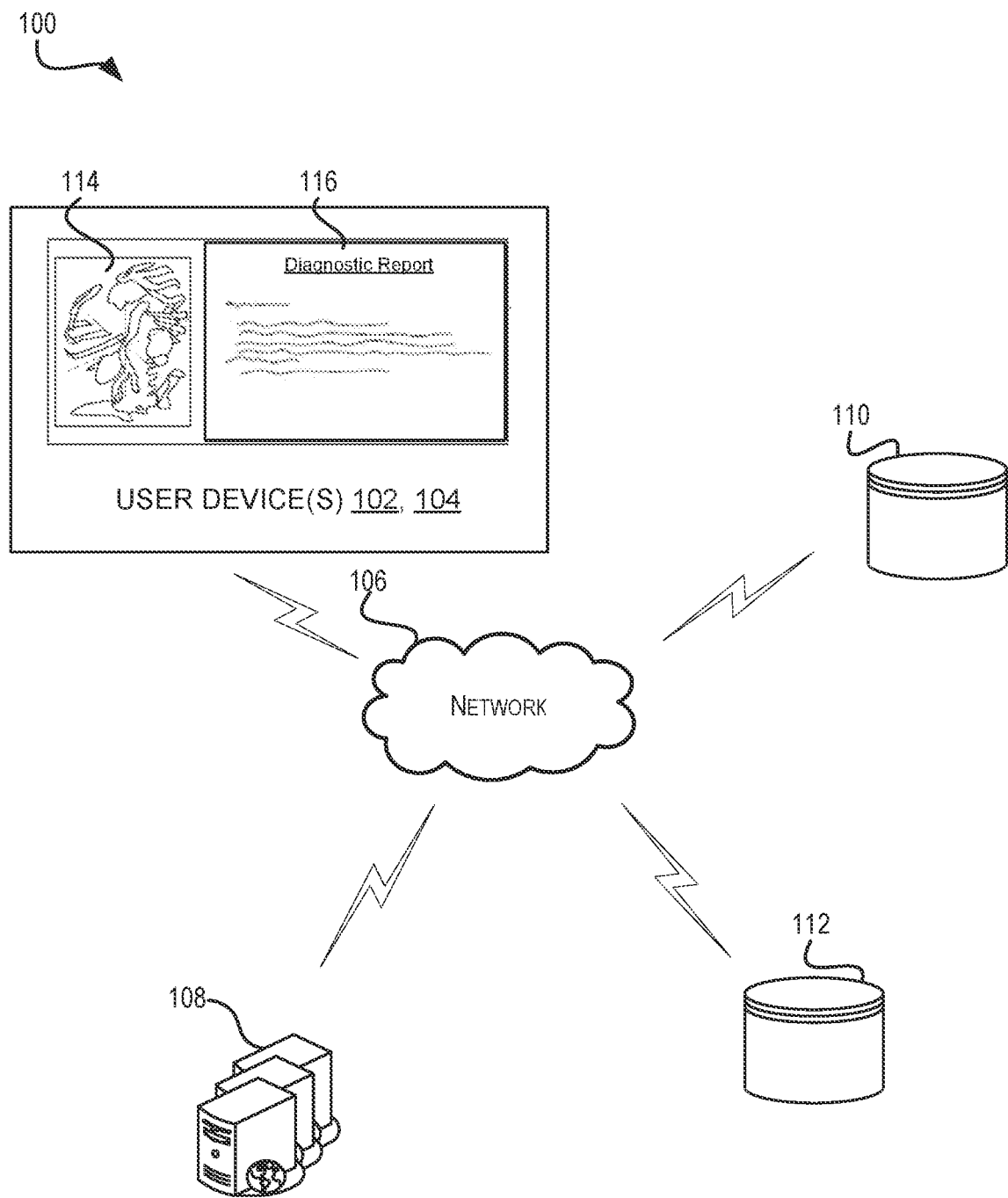
FIG. 1 illustrates a system for generating medical image based medical reports, according to at least some examples.

Turning now to the figures in which similar reference identifiers refer to similar elements in the various figures, FIG. 1 illustrates an example system diagram for elements of a system 100 for generating a medical image based medical report. The system 100 includes one or more user devices 102, 104, an application server 108, a first database 110, and a second database 112. The system 100 includes a network 106 that provides communication between the various elements. The network 106 may be wired or wireless and may include elements such as the internet. Initially, medical images of a patient are stored on the first database 110 awaiting analysis by a healthcare professional and generation of a medical report. When the healthcare professional begins working on a particular case, the healthcare professional accesses image data for the case from the first database 110 over the network 106. A medical image 114 defined by the image data is viewable on the user device 104 using systems and methods described herein for reference by the healthcare professional during preparation of the medical report.

The one or more user devices 102, 104 can be any suitable single user device or include any suitable combination of suitable user devices. For example, suitable single user devices that can be used include, but are not limited to, a desktop computer, a laptop computer, a smart phone, a tablet, etc. Suitable combinations of suitable user devices include, but are not limited to, a smart phone and a desktop computer, a smart phone and a laptop computer, a smart phone and a tablet, etc. When the one or more user devices 102, 104 include a suitable combination of suitable user devices, the user devices 102 104 can be in communication with one another such that the user device 102 may be used to control some actions with respect to the generation of the medical report on the user device 104. For example, the user device 102 can be a smartphone and the user device 104 can be a personal computer. The user device 102 can meet FDA and other requirements including privacy requirements and secure patient information as part of the system. The user device 102 can include a voice input device. The user device 102 can have a graphical user interface ("GUI") that presents options for the healthcare professional to interact with the medical report generation software on the user device 104.

Through the one or more user devices 102, 104, the healthcare professional is able to generate a medical report 116 based on the medical image 114 by dictating content and/or report generation instructions into the one or more user devices 102, 104 and/or keyboard entry of content and/or report generation instructions via the one or more user devices 102, 104. The medical report 116 can be generated in real-time either based on natural language processing of commands included in the dictation, or by determining, based on the contents of the dictated information from the user, a report format and information such as image information to be included in the medical report 116.

In some examples, the one or more user devices 102, 104 perform the functions of the techniques and methods described herein. In some examples, processing of data or some operations is performed by the application server 108, such as a cloud computing device or remote server. In some examples, processing is distributed and shared between the one or more user devices 102, 104 and the application server 108.

Following generation, the medical report 116 is exported to the second database 112 for storage and later access in connection with treatment of the patient. The second database 112 can be part of the first database 110.

Medical images of a patient are typically obtained via a medical imaging device. The medical imaging device can include any suitable device for imaging a patient to generate corresponding image data. The imaging device can include x-ray machines, computed tomography machines, magnetic resonance imaging machines, or other such imaging devices. The image data generated by the imaging device can be stored in a database for access by a healthcare professional. The healthcare professional can review medical images of the patient and prepare a medical report for the patient by dictating and/or typing the medical report using a medical report generation system such as the system 100. The medical report 116 can include findings and notes of the healthcare professional based on the medical image 114. The medical report 116 can be subsequently stored in a database. A healthcare professional can then access the report from the database to decide on treatment for the patient.

Error and Omission Detection

FIG. 2, FIG. 3, FIG. 4, and FIG. 5 illustrate a collection of processes 200, 300, 400, 500 that can be employed in the system 100 for generating a medical image based medical report. The system 100 can employ all possible combinations of the processes 200, 300, 400, 500. As describe herein, each of the processes 200, 300, 400, 500 provides for detection of potential errors and potential omissions during the preparation of a medical image based medical report and provides corresponding feedback to a healthcare professional to facilitate correction of the medical report by the healthcare professional. In many embodiments, the feedback is provided prior to completion of the medical report thereby facilitating reduction of errors and omissions in the resulting medical image based diagnostic report. Some or all of the processes 200, 300, 400, 500 (or any other processes described herein, or variations, and/or combinations thereof) can be performed under the control of one or more computer systems configured with executable instructions and can be implemented as code (e.g., executable instructions, one or more computer programs, or one or more applications) executing collectively on one or more processors, by hardware or combinations thereof. The code can be stored on a computer-readable storage medium, for example, in the form of a computer program that includes instructions executable by one or more processors. The computer-readable storage medium can be non-transitory. In some embodiments, the system 100 is configured to perform the process 200, the process 300, the process 400, and/or the process 500.

Figure 2:
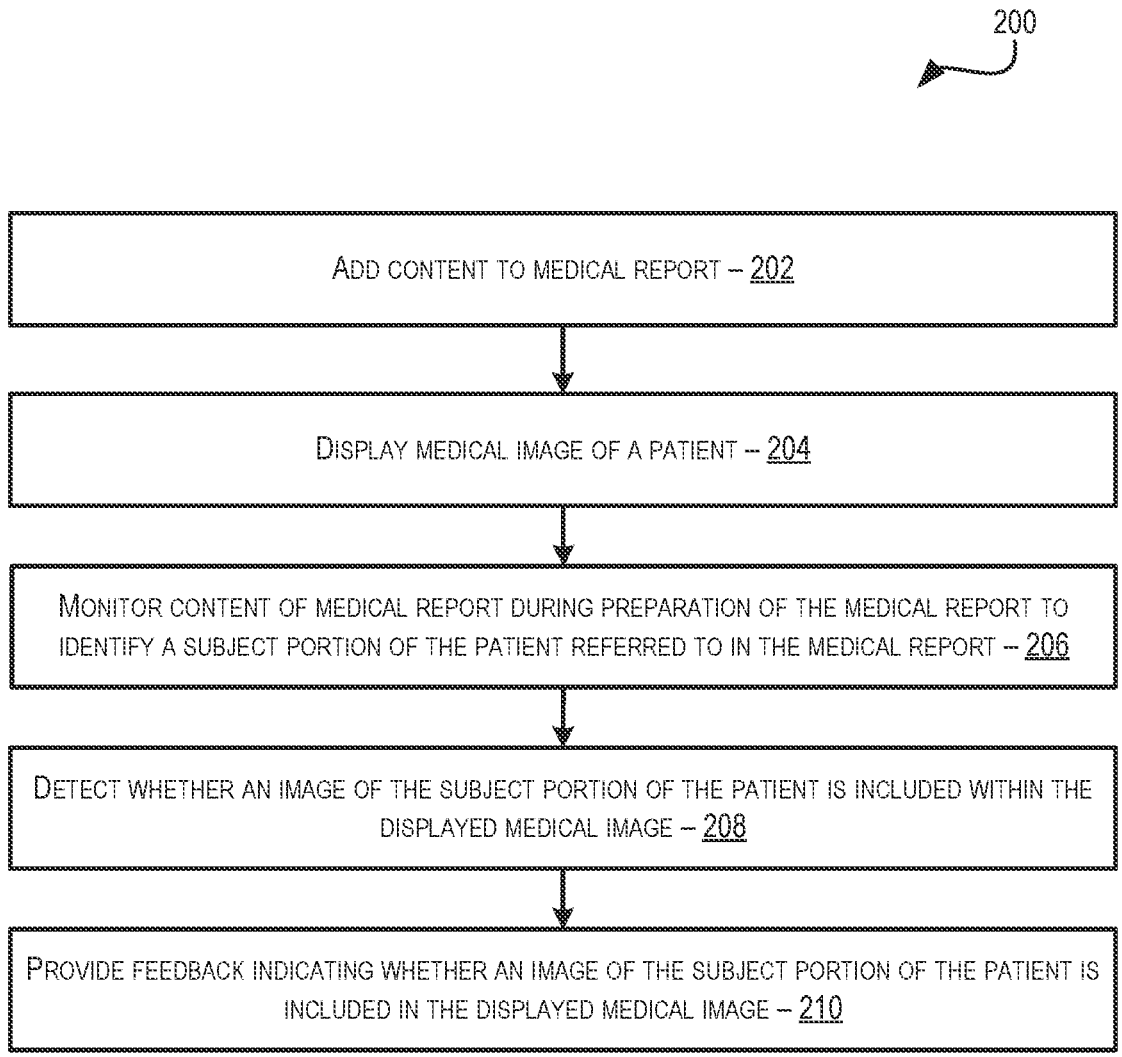
FIG. 2 is a flow diagram illustrating an example process, which can be accomplished via the system of FIG. 1, of providing feedback during preparation of a medical report regarding whether content of the medical report is consistent with a medical image of a patient.

FIG. 2 is a flow diagram illustrating an example process 200, which can be accomplished via the system 100, of providing feedback during preparation of a medical report regarding whether content of the medical report is consistent with a medical image of a patient. The process 200 provides feedback indicative of a potential identification error (e.g., organ identification error) during preparation of a medical report, according to at least some examples. In act 202, content is added to a medical report. The content can be added to the medical report using any suitable device(s), such as the one or more user devices 102, 104. In act 204, a medical image of a patient is displayed. The medical image can be displayed on any suitable device. For example, in the system 100, a medical image 114 is displayed on the user device 104. In many instances, the medical image is displayed for viewing by a healthcare professional for analysis by the healthcare professional during preparation of medical diagnostic report (e.g., the medical diagnostic report 116) based on the displayed medical image.

In act 206, the contents of the medical report are monitored by a computer system (e.g., the computer system 100) during preparation of the medical report to identify an organ(s) and/or portion(s) of the particular patient referred to in the medical report. Any suitable approach can be used to identify the organ(s) and/or the portion(s) of the patient referred to in the medical report. For example, words in the medical report can be compared to a list of organs and/or portions of a patient by the computer system to monitor for the occurrence of any of the organs and/or portions of a patient on the list. As one example, the occurrence of "right kidney" in the medical report can be identified by the computer system as a subject organ of the medical report where the list of organs and/or portions of the patient include "right kidney."

In many embodiments, a check is made by the computer system to determine whether the organ or portion of the patient referred to in the medical report (as identified in act 206) is shown in the medical image. In some instances, based on assessment of the medical image by the computer system, a determination is made by the computer system whether the medical image includes an image of the organ or portion of the patient referred to in the medical report (act 208). Any suitable approach can be used by the computer system to assess the contents of the medical image. For example, one or more trained computer visions algorithms can be used by the computer system to identify and localize images of organs and/or portions of the patient shown in the medical image.

In act 210, feedback is provided by the computer system to the healthcare professional preparing the report indicating whether an image of the subject portion of the patient referred to in the medical report is included in the displayed medical image. For example, in instances where the organ or portion of the patient referred to in the medical report is not shown in the medical image, negative feedback can be provided indicating that the referred to organ or portion of the patient is not shown in the medical image. The negative feedback can take any suitable form. For example, one or more portions of the medical report that refer to the organ or portion of the patient can be designated in a suitable manner (e.g., highlighted in red, underlined, shown in bold, etc.) to bring the discrepancy to the attention of the healthcare professional preparing the medical report. As another example, in instances where the organ or portion of the patient referred to in the medical report is shown in the medical image, positive feedback can be provided indicating that the referred to organ or portion of the patient is shown in the medical image. The positive feedback can take any suitable form. For example, one or more portions of the medical report that refer to the organ or portion of the patient can be designated in a suitable manner (e.g., highlighted in green, underlined, shown in bold, etc.) to inform the healthcare professional that the organ or portion of the patient referred to in the medical report is shown in the displayed medical image. Additionally, a portion of the displayed medical image corresponding to the organ or portion of the patient referred to in the medical report can be designated in a suitable manner (e.g., highlighted, outlined, shown in a different color, etc.) so that the healthcare professional is made aware what portion of the displayed medical image corresponds to the organ or portion of the patient referred to in the medical report.

Figure 3:
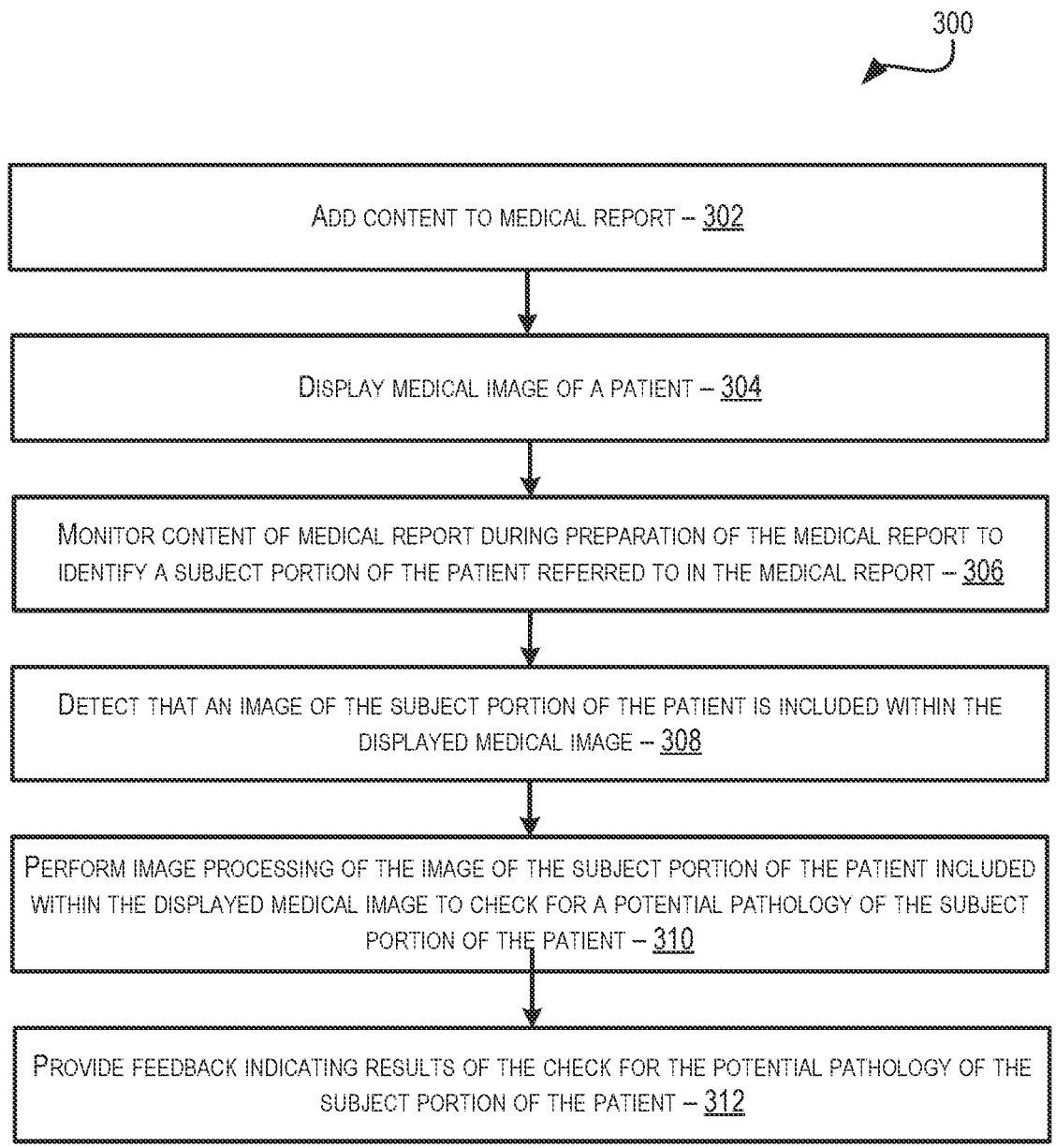
FIG. 3 is a flow diagram illustrating an example process, which can be accomplished via the system of FIG. 1, of performing image processing of a medical image of a patient to check for a potential pathology in a portion of the patient referred to in a medical report during preparation of the medical report.

FIG. 3 is a flow diagram illustrating an example process 300, which can be accomplished via the system 100, of performing image processing of a medical image of a patient to check for a potential pathology in a portion of the patient referred to in a medical report during preparation of the medical report. In act 302, content is added to a medical report. The content can be added to the medical report using any suitable device(s), such as the one or more user devices 102, 104. In act 304, a medical image of a patient is displayed. The medical image can be displayed on any suitable device such as described herein with respect to act 204.

In act 306, the contents of the medical report are monitored by a computer system (e.g., the computer system 100) during preparation of the medical report to identify an organ(s) and/or portion(s) of the particular patient referred to in the medical report. Any suitable approach can be used to identify the organ(s) and/or the portion(s) referred to in the medical report such as described herein with respect to act 206.

In act 308, the computer system detects that an image of an organ or portion of the patient referred to the in medical report (as identified in act 206) is shown in the medical image. Any suitable approach can be used by the computer system to detect that an image of an organ or portion of the patient referred to the in medical report (as identified in act 206) is shown in the medical image. For example, one or more trained computer visions algorithms can be used by the computer system to identify and localize images of organs and/or portions of the patient shown in the medical image.

In act 310, the computer system performs targeted image processing of the image of the organ or portion of the patient referred to in the medical report that is shown in the medical image to check for a potential pathology of the organ or portion of the patient. The targeted image processing performed can be specialized to the particular organ or portion of the patient.

In act 312, the computer system provides feedback to the healthcare professional preparing the medical report indicating the results of the check for the potential pathology. In instances where a potential pathology is identified via the targeted image processing, the feedback can inform the healthcare professional of the potential pathology identified. The feedback can include, for example, a suitable designation of a portion of the displayed medical image corresponding to the identified potential pathology and/or outputting of a suitable message to the healthcare professional that identifies and/or describes the identified potential pathology in the subject organ or portion of the patient. In instances where no potential pathology is identified via the targeted image processing, the feedback can inform the healthcare professional that the targeted image processing did not identify any potential pathology of the subject organ or portion of the patient. By including automated image processing based checks for potential pathologies in organ(s) or portion(s) of a patient shown in the displayed medical image, omission of a potential pathology, that is discernable from the displayed medical image, in the medical report may be reduced.

Figure 4:
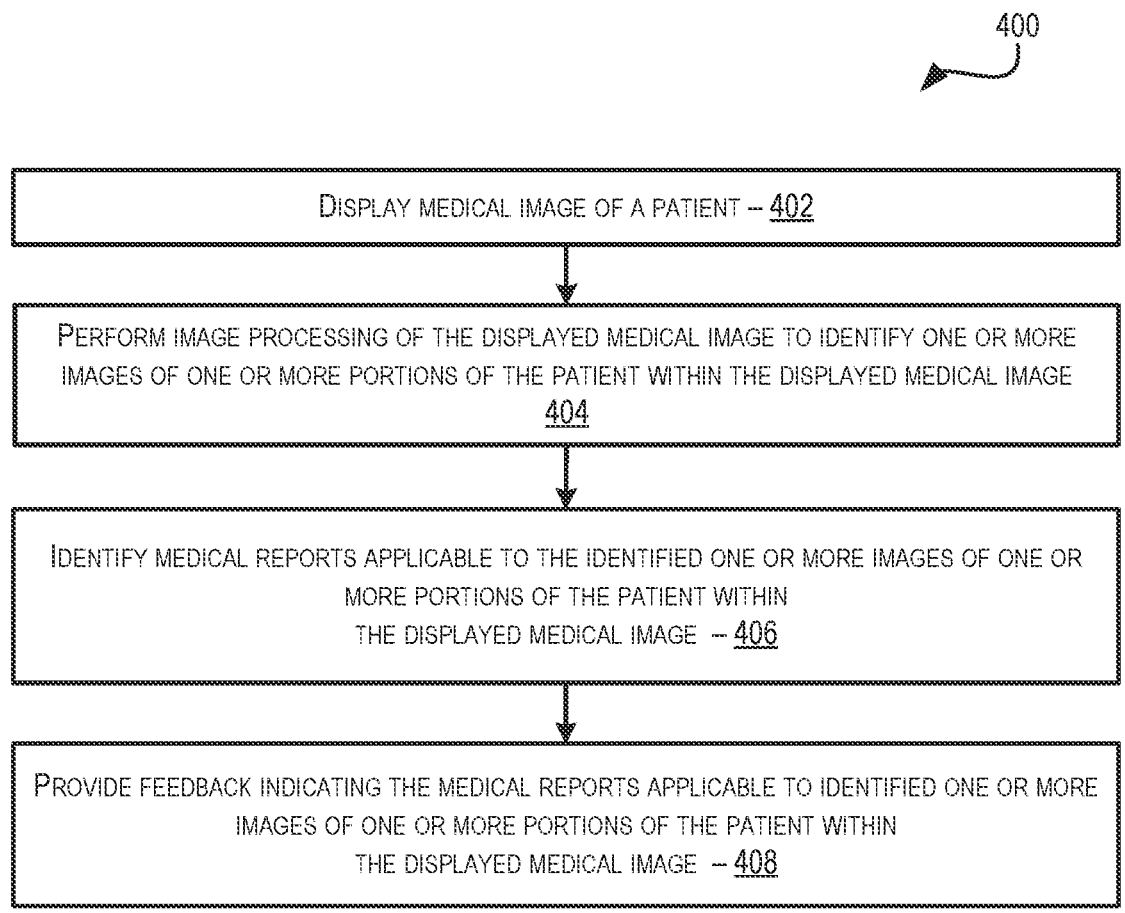
FIG. 4 is a flow diagram illustrating an example process, which can be accomplished via the system of FIG. 1, of providing feedback indicating medical reports applicable to one or more portions of a patient shown in a medical image of a patient.

FIG. 4 is a flow diagram illustrating an example process 400, which can be accomplished via the system 100, of providing feedback indicating medical reports applicable to one or more portions of a patient shown in a medical image of a patient. In act 402, a medical image of a patient is displayed. The medical image can be displayed on any suitable device such as described herein with respect to act 202.

In act 404, the contents of the medical report are monitored by a computer system (e.g., the computer system 100) during preparation of the medical report to identify an organ(s) and/or portion(s) of the particular patient referred to in the medical report. Any suitable approach can be used to identify the organ(s) and/or the portion(s) referred to in the medical report such as described herein with respect to act 204.

In act 406, the computer system identifies medical reports applicable to the identified organ(s) or portion(s) of the patient referred to in the medical report. For example, for each organ or portion of a patient in a suitable overall list of possible organs or portions of a patient, the computer system can store a list of one or more applicable medical reports. For each identified organ or portion of the patient referred to in the medical report, the computer system can identify the applicable medical report(s) as corresponding to the stored list of one or more medical reports applicable to the identified organ or portion of the patient.

In act 408, the computer system provides feedback to the healthcare professional preparing the medical report that indicates the one or more medical reports applicable to the identified organ(s) or portion(s) of the patient in the displayed medical image. In some embodiments, the computer system presents a limited selection consisting of the applicable medical reports to the healthcare professional that can be prepared by the healthcare professional with reference to the displayed medical image, thereby preventing the preparation of a medical report type that is not applicable to the displayed medical image. In some embodiments, the computer system provides feedback to the healthcare professional that indicates the applicable medical reports, but does limit the type of medical report that can be selected by the healthcare professional for completion with regard to the displayed medical image.

Figure 5:
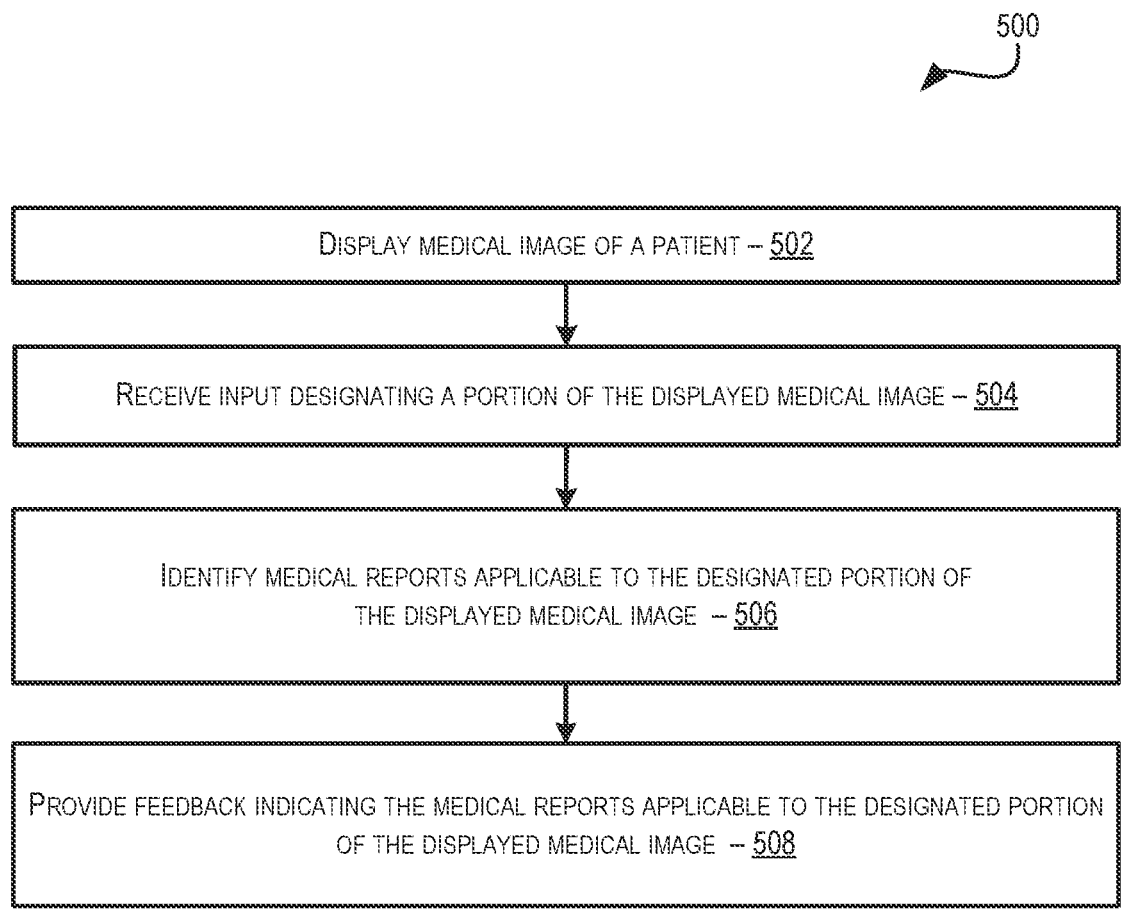
FIG. 5 is a flow diagram illustrating an example process, which can be accomplished via the system of FIG. 1, of providing feedback indicating medical reports applicable to a designated portion of a medical image.

FIG. 5 is a flow diagram illustrating an example process 500, which can be accomplished via the system 100, of providing feedback indicating medical reports applicable to a designated portion of a medical image. In act 502, a medical image of a patient is displayed. The medical image can be displayed on any suitable device such as described herein with respect to act 202.

In act 504, the computer system receives an input from the healthcare professional that designates a portion of the displayed medical image. Any suitable approach can be used to input the designation of the portion of the displayed medical image. In some embodiments, an input device of the user device 104 (e.g., computer mouse, touch screen, etc.) can be used to designate or otherwise select a portion of the displayed medical image.

In act 506, the computer system processes the input to identify one or more medical reports applicable to the designated portion of the displayed medical image. In some embodiments, the computer system processes the input to identify one or more organs or portions of the patient corresponding to the input designating the portion of the displayed medical images. Any suitable approach can be used by the computer system to assess the contents of the designated portion of the displayed medical image. For example, one or more trained computer visions algorithms can be used by the computer system to identify and localize images of organs and/or portions of the patient shown in the designated portion of the displayed medical image. The computer system can store data that specifies one or more medical reports applicable to each of applicable organs or portions of the patient and use the data to identify the one or more medical reports applicable to the designated portion of the displayed medical image. In act 508, the computer system provides feedback to the healthcare professional preparing the medical report that indicates the one or more medical reports applicable to the designated portion of the displayed medical image. In some embodiments, the computer system presents a limited selection consisting of the applicable medical reports to the healthcare professional that can be prepared by the healthcare professional with reference to the designated portion of the displayed medical image, thereby preventing the preparation of a medical report type that is not applicable to the designated portion of the displayed medical image. In some embodiments, the computer system provides feedback to the healthcare professional that indicates the medical reports applicable to the designated portion of the displayed medical image, but does limit the type of medical report that can be selected by the healthcare professional for completion with regard to the designated portion of the displayed medical image.

Figure 6:
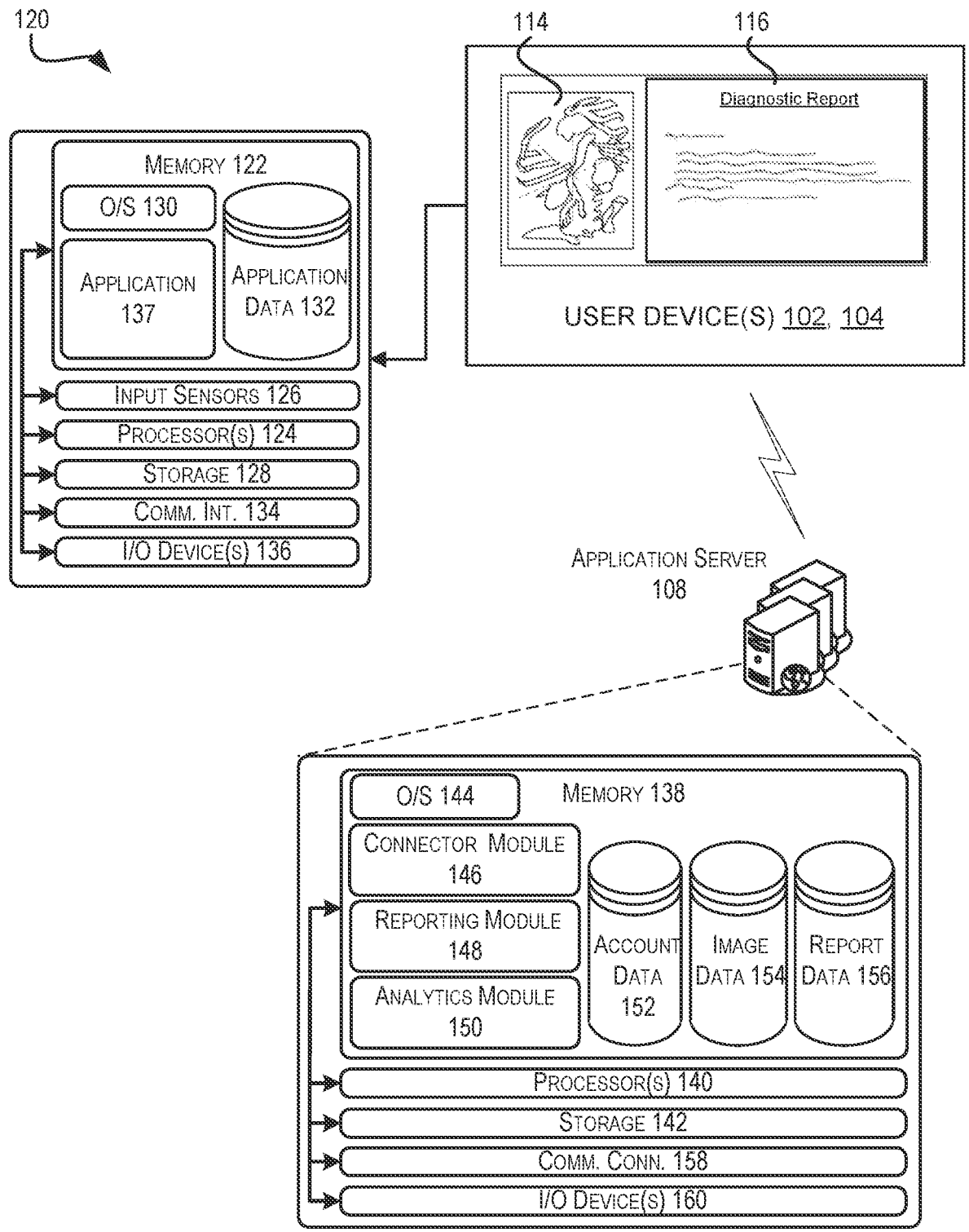
FIG. 6 illustrates an example system diagram for elements of the system for generating a medical report of FIG. 1.

FIG. 6 illustrates an example configurations of the one or more user devices 102, 104 and the application server 108 of the system 100 for generating a medical image based medical report. The one or more user devices 102, 104 can be in communication with a number of other components, including at least the application server 108. The application server 108 can perform at least a portion of the processing functions of an application installed on the one or more user devices 102, 104.

The one or more user devices 102, 104 can be any suitable electronic device that is capable of providing at least a portion of the capabilities described herein. In particular, the one or more user devices 102, 104 can be any electronic device(s) capable of receiving data from a remote database and input devices, displaying information to a user (e.g., a healthcare professional), and outputting data to a database. In some embodiments, the one or more user devices 102, 104 are capable of establishing a communication session with another electronic device (e.g., the application server 108) and transmitting to and receiving data from the electronic device. The one or more user devices 102, 104 can have the ability to download and/or execute applications. The one or more user devices 102, 104 can include mobile communication devices as well as personal computers and thin-client devices. The one or more user devices 102, 104 can include any portable electronic device that has a primary function related to communication. For example, the one or more user devices 102, 104 can include a smart phone, a personal data assistant (PDA), or any other suitable handheld device. The one or more user devices 102, 104 can be implemented as a self-contained unit with various components (e.g., input sensors, one or more processors, memory, etc.) integrated into the one or more user devices 102, 104. Reference in this disclosure to an "output" of a component or an "output" of a sensor does not necessarily imply that the output is transmitted outside of the one or more user devices 102, 104. Outputs of various components can remain inside a self-contained unit that defines the one or more user devices 102, 104.

In one illustrative configuration, the one or more user devices 102, 104 include at least one memory 122 and one or more processing units (or processor(s)) 124. The processor(s) 124 can be implemented as appropriate in hardware, computer-executable instructions, firmware or combinations thereof. Computer-executable instruction or firmware implementations of the processor(s) 124 can include computer-executable or machine executable instructions written in any suitable programming language to perform the various functions described. The one or more user devices 102, 104 can include one or more input sensors 126 for receiving user and/or environmental input such as speech input and user interactions with a user interface. There can be a variety of input sensors 126 capable of detecting user or environmental input, such as an accelerometer, a camera device, a depth sensor, a microphone, a global positioning system (e.g., GPS) receiver, etc.

The memory 122 can store program instructions that are loadable and executable on the processor(s) 124, as well as data generated during the execution of these programs. Depending on the configuration and type of the one or more user devices 102, 104, the memory 122 can be volatile (such as random access memory (RAM)) and/or non-volatile (such as read-only memory (ROM), flash memory, etc.). The one or more user devices 102, 104 can include additional storage 128, such as either removable storage or non-removable storage including, but not limited to, magnetic storage, optical disks, and/or tape storage. The disk drives and their associated computer-readable media can provide non-volatile storage of computer-readable instructions, data structures, program modules, and other data for the computing devices. In some implementations, the memory 122 includes multiple different types of memory, such as static random access memory (SRAM), dynamic random access memory (DRAM) or ROM. Turning to the contents of the memory 122 in more detail, the memory 122 can include an operating system 130 and one or more application programs or services for implementing the features disclosed herein including at least an application 137. The memory 122 can store application data 132, which provides information to be generated by and/or consumed by the application 137. In some embodiments, the application data 132 is stored in a database.

For the purposes of this disclosure, an application 137 can include any set of computer executable instructions installed upon, and executed from, the one or more user devices 102, 104. The application 137 can be installed on the one or more user devices 102, 104 by a manufacturer(s) of the one or more user devices 102, 104 or by another entity(s). In some embodiments, the application 137 causes the one or more user devices 102, 104 to establish a communication session with the application server 108 that provides backend support for the application 137. An application server 108 can maintain account information associated with particular one or more user devices 102, 104 and/or user(s) (e.g., healthcare professional(s)). In some embodiments, a user can be required to log into the application 137 in order to access functionality provided by the application 137.

In accordance with at least some embodiments, the application 137 is configured to provide a graphical user interface (GUI) enabling generation of a medial image based medical report in accordance with the methods described herein. In accordance with at least some embodiments, the application 137 receives output from the input sensors 126 and identifies speech, user interactions, annotations, or potential objects within that output. For example, the application 137 can receive a speech generated output signal from a microphone, such as the microphone previously described with respect to input sensors 126. The application 137 can be configured to transcribe the speech generated output signal and generate report information based on the speech generated output signal. For example, speech input can include notes to be transcribed and included in a report. In another example, the application 137 can utilize one or more computer vision algorithms to identify anatomy in the displayed medical image. In this example, the application 137 can receive image information from an image database 154 of the application server 108 and annotations or user inputs through the input sensors 126 as the user interacts with the image data. In some embodiments, the application 137 causes the one or more user devices 102, 104 to transmit the output obtained from the input sensors 126 to the application server 108, which may then perform one or more natural language processing techniques or computer vision techniques upon that output for respective speech input or user inputs related to the image data.

The one or more user devices 102, 104 can include communications interface(s) 134 that enable the one or more user devices 102, 104 to communicate with any other suitable electronic devices. In some examples, the one or more user devices 102, 104 include multiple user devices 102, 104 in communication with one another, such as a personal computer and a mobile device in communication with one another. In some examples, the communication interface 134 is configured for communication between the one or more user devices 102, 104 and other electronic devices on a network (e.g., on a private network). For example, the one or more user devices 102, 104 can include a Bluetooth wireless communication module, which allows the one or more user devices 102, 104 to communicate with another electronic device (e.g., a Bluetooth laser measuring tape, etc.). The one or more user devices 102, 104 can include input/output (I/O) device(s) and/or ports 136, such as for enabling connection with a keyboard, a mouse, a pen, a voice input device, a touch input device, a display, speakers, a printer, etc.

In some embodiments, the one or more user devices 102, 104 communicate with the application server 106 via the communication network 106. The communication network 106 can include any one or a combination of many different types of networks, such as cable networks, the Internet, wireless networks, cellular networks, and other private and/or public networks. In addition, the communication network 106 can include multiple different networks. For example, the one or more user devices 102, 104 can use a wireless local area network ("WLAN") to communicate with a wireless router, which may then route the communication over a public network (e.g., the Internet) to the application server 108.

The application server 108 can include any computing device or plurality of computing devices configured to perform one or more calculations on behalf of the application 137 on the one or more user devices 102, 104. In some embodiments, the application 137 can be in periodic communication with the application server 108. For example, the application 137 can receive updates, push notifications, or other instructions from the application server 108. In some embodiments, the application 137 and application server 108 use a proprietary encryption and/or decryption scheme to secure communications between the application 137 and the application server 108. In some embodiments, the application server 108 can be implemented by one or more virtual machines implemented in a hosted computing environment. The hosted computing environment can include one or more rapidly provisioned and released computing resources, which can include computing, networking, and/or storage devices. A hosted computing environment may also be referred to as a cloud-computing environment.

In one illustrative configuration, the application server 108 includes at least one memory 138 and one or more processing units (or processor(s)) 140. The processor(s) 140 can be implemented as appropriate in hardware, computer-executable instructions, firmware or combinations thereof. Computer-executable instruction or firmware implementations of the processor(s) 140 can include computer-executable or machine executable instructions written in any suitable programming language to perform the various functions described.

The memory 138 can store program instructions that are loadable and executable on the processor(s) 140, as well as data generated during the execution of these programs. Depending on the configuration and type of application server 108, the memory 138 can be volatile (such as random access memory (RAM)) and/or non-volatile (such as read-only memory (ROM), flash memory, etc.). The application server 108 can include additional storage 142, such as either removable storage or non-removable storage including, but not limited to, magnetic storage, optical disks, and/or tape storage. The disk drives and their associated computer-readable media can provide non-volatile storage of computer-readable instructions, data structures, program modules, and other data for the computing devices. In some implementations, the memory 138 includes multiple different types of memory, such as static random access memory (SRAM), dynamic random access memory (DRAM) or ROM.

Turning to the contents of the memory 138 in more detail, the memory 138 can include an operating system 144 and one or more application programs or services for implementing the features disclosed herein including at least a module for receiving image data and outputting or encoding a report for output (connector module 146) and/or a module for producing expressive reports that include text, images, tables, measurements, and other such data (reporting module 148) and/or a module for advanced language, speech, and image analysis services (analytics module 150). The memory 138 can include account data 152, which provides information associated with user accounts maintained by the described system, image data 154, which includes medical image data gathered and stored from medical imaging devices, and/or report data 156, which stores and provides information on a number of reports including completed reports and pending reports. In some embodiments, one or more of the account data 152, the image data 154, or the report data 156 can be stored in a database.

The memory 138, memory 122, and the additional storage 142, both removable and non-removable, are examples of computer-readable storage media. The computer-readable storage media can include volatile or non-volatile, removable or non-removable media implemented in any method or technology for storage of information such as computer-readable instructions, data structures, program modules or other data. As used herein, the term "modules" can refer to programming modules executed by computing systems (e.g., processors) that are installed on and/or executed by the application server 108. The application server 108 can include communications connection(s) 158 that allow the application server 108 to communicate with a stored database, another computing device or server, user terminals, and/or other components of the described system. The application server 108 can include input/output (I/O) device(s) and/or ports 160, such as for enabling connection with a keyboard, a mouse, a pen, a voice input device, a touch input device, a display, speakers, a printer, etc.

Turning to the contents of the memory 138 in more detail, the memory 138 can include the connector module 146, the reporting module 148, the analytics module 150, the database containing account data 152, the database containing image data 154, and/or the database containing report data 156.

In some embodiments, the connector module 146 is configured to, in conjunction with the processor(s) 140, receive image data from the image data 154, receive input sensor data from the one or more user devices 102, 104, and output reports to report data 156. The connector module 146 can be interoperable between various systems and databases according to Digital Imaging and Communication in Medicine ("DICOM(R)") and Health Level 7 ("HL7"), which provide frameworks and related standards for the exchange, integration, sharing, and retrieval of electronic health data. The connector module 146 can output the report into any suitable format accessible by operators, for example including a JavaScript Object Notation (JSON) format such that embedded images within the report may be encoded to be compatible with existing systems that may typically only provide viewing of text-only reports.

In some embodiments, the reporting module 148 is configured to, in conjunction with the processor(s) 140, receive, edit, and produce reports including text, images, tables, and measurements. The reporting module 148 can interface with third party viewers, such as web-based image viewers and editing software. The reporting module 148 can receive inputs from the input sensors 126 as well as the analytics module 150 and image data 154 to generate a report. The reporting module 148 can interface with the connector module 146 to receive as well as output information to various systems and databases.

In some embodiments, the analytics module 150 is configured to, in conjunction with the processor(s), provide language, speech, and image analysis for use by the reporting module 148 and access by the user via the one or more user devices 102, 104 in generating the report. The analytics module 150 can provide speech transcription, image classification, anatomy localization, vertebrae localization and labeling, image alignment, interactive segmentation and measurement of anatomy, among other speech, text, and image analysis processing.

The analytics module 150 can provide speech-to-text transcription to transform speech input data received through input sensor 126 into text. In some embodiments, the analytics module 150 interfaces with external transcription services, including transcription services optimized for medical applications. In some embodiments, the analytics module 150 includes a machine learning algorithm trained using medical terminology to transcribe speech input into text data. The analytics module 150 can include natural language processing algorithm(s) to determine medical terms, entities, relations, ontologies, in addition to determining natural language recognition capable of identifying imperative commands, such as commands from the user instructing the reporting module 148 to generate, revise, edit, or produce at least a portion of a medical report. In some examples, the analytics module 150 provides utterance understanding and perform actions, or cause the processor 140 to perform actions based on speech input and parse report data from imperative commands to transcribe and incorporate transcribed report data into the report without any particular indication by the user. In such examples, the user can dictate a string of information such as describing a particular abnormality in the displayed medical image.

The analytics module 150 can include one or more computer vision algorithms configured for detection of anatomy and abnormalities. The one or more computer vision algorithms can be configured to focus on general tasks including detection of anatomy and abnormalities and can include specific computer vision algorithms for detecting or identifying disease-specific tasks (such as detecting particular tumors). In some examples, the analytics module 150 includes an image segmentation algorithm for interactive delineation and measurement of any generic structure of interest in two- and three-dimensions. Image segmentation algorithms can be used to compute and report volumes and linear measurements according to user interactions with the GUI. The analytics module 150 can include an image modality classification algorithm that recognizes a modality of the medical images (e.g., CT, CT angiogram, MR T1, MR T2, MR T1-contrast, MR and FLAIR). The modality classification information can be included in the report and can be used to select a particular computer vision algorithm for performing relevant measurements and detection. The analytics module 150 can include an anatomical view classification that recognizes a viewed anatomical region in the image data. The anatomical view classification may be useful for further identifying specific organs and additional anatomy in the image data and may also be useful for selecting further computer vision algorithms. The analytics module 150 can include an organ localization algorithm that generated bounding boxes around organs in the displayed medical image. The analytics module 150 can include a vertebrae labeling algorithm that detects each vertebra in image data and names the vertebra according to the standard anatomical naming convention for vertebrae. The analytics module 150 can include a study alignment algorithm that registers and maps image data gathered at different points in time for comparison of a particular portion of the patient over a period of time, for example to track the progression of treatment. The analytics module 150 can include an anomaly segmentation algorithm that localizes and segments generic anomalies in the displayed medical image. The anomaly segmentation algorithm can be configured for detection and identification of anomalies without specific diagnosis of the type of abnormality, as such a determination may be made by a radiologist. In some examples, the analytics module 150 includes additional algorithms including computer vision algorithms, language processing algorithms, and other such algorithms for processing image, speech, text, and other data.

Figure 7:
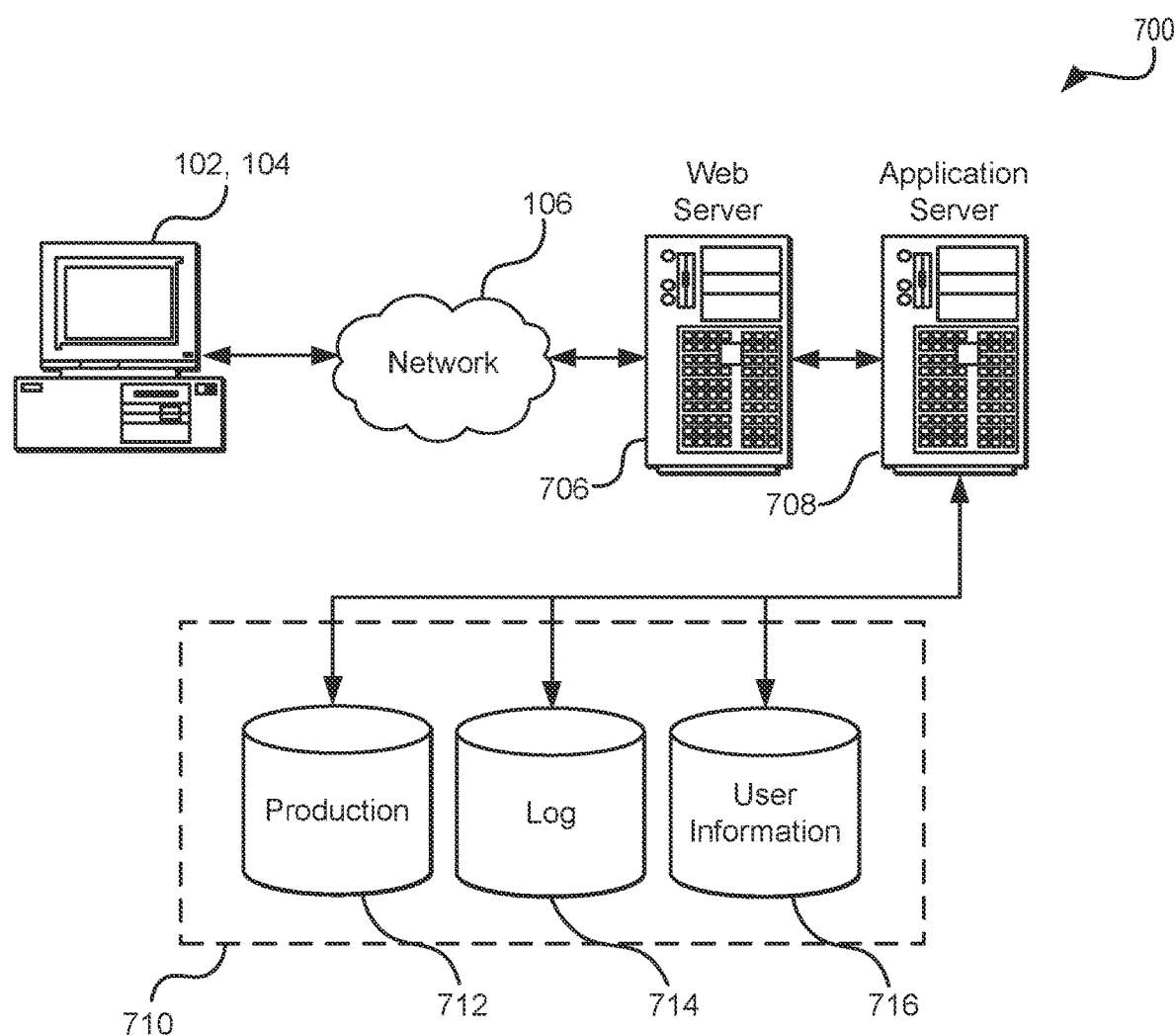
FIG. 7 illustrates an environment in which various embodiments can be implemented.

FIG. 7 illustrates an environment in which various embodiments can be implemented.

FIG. 7 illustrates aspects of an example environment 700 for implementing aspects in accordance with various embodiments. As will be appreciated, although a Web-based environment is used for purposes of explanation, different environments may be used, as appropriate, to implement various embodiments. The environment includes the one or more electronic user devices 102, 104, which can include any appropriate device operable to send and receive requests, messages, or information over the network 106 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 706 for receiving requests and serving content in response thereto, although for other networks an alternative device serving a similar purpose could be used as would be apparent to one of ordinary skill in the art.

The illustrative environment includes at least one application server 708 and a data store 710. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the one or more user device 102, 104 and the application server 708, can be handled by the Web server. It should be understood that the Web and application servers are not required and are merely example components, as structured code discussed herein can be executed on any appropriate device or host machine as discussed elsewhere herein.

The data store 710 can include several separate data tables, databases or other data storage mechanisms and media for storing data relating to a particular aspect. For example, the data store illustrated includes mechanisms for storing production data 712 and user information 716, which can be used to serve content for the production side. The data store also is shown to include a mechanism for storing log data 714, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 710. The data store 710 is operable, through logic associated therewith, to receive instructions from the application server 708 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the one or more user devices 102, 104. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 7. Thus, the depiction of the system 700 in FIG. 7 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGP") servers, data servers, Java servers, and business application servers. The server(s) also may be capable of executing programs or scripts in response to requests from user devices, such as by executing one or more Web applications that may be implemented as one or more scripts or programs written in any programming language, such as Java °, C, C #, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for preparing a medical report, the system comprising:
    one or more displays operable to display a medical image of a patient;
    one or more input devices;
    one or more processors; and
    one or more computer-readable media that store non-transitory instructions executable by the one or more processors to cause the one or more processors to:
        receive image data for a medical image of a patient, wherein the image data is generated via a medical imaging system;
        cause the one or more displays to display the medical image of the patient;
        receive user input for preparation of the medical report via the one or more input devices;
        display content of the medical report via the one or more displays during preparation of the medical report;
        identify a subject organ of the patient referred to in the medical report by monitoring content of the medical report during preparation of the medical report;
        process the image data to detect whether an image of the subject organ of the patient is included in the displayed medical image of the patient; and
        output feedback via the one or more displays that indicates whether an image of the subject organ of the patient is included in the displayed medical image of the patient.

2. A system of claim 1, wherein the non-transitory instructions are further executable by the one or more processors to cause the one or more processors to:
    process the image data to detect and localize one or more images of a corresponding one or more organs of the patient in the displayed medical image of the patient; and
    determine whether the one or more images of the corresponding one or more organs of the patient in the displayed medical image of the patient do not include an image of the subject organ.

3. A system of claim 1, wherein the non-transitory instructions are further executable by the one or more processors to cause the one or more processors to:
    perform image processing of the image data to check for a potential pathology of an organ imaged in the displayed medical image of the patient; and
    output feedback indicative of a result of the check for the potential pathology of the organ imaged in the displayed medical image of the patient.

4. A system of claim 1, wherein the non-transitory instructions are further executable by the one or more processors to cause the one or more processors to display a designation of the subject organ in the displayed medical image of the patient.

5. A system for preparing a medical report, the system comprising:
    one or more displays operable to display a medical image of a patient;
    one or more processors; and
    one or more computer-readable media that store non-transitory instructions executable by the one or more processors to cause the one or more processors to:
        receive image data for a medical image of a patient, wherein the image data is generated via a medical imaging system;
        display the medical image of the patient via the one or more displays;
        monitor content of the medical report during preparation of the medical report;
        process the image data to detect one or more organs of the patient imaged in the displayed medical image of the patient;
        compare the content of the medical report with the one or more organs imaged in the displayed medical image of the patient to detect one or more potential errors in the medical report; and
        output feedback indicative of the one or more potential errors in the medical report.

6. A system of claim 5, wherein:
    the processing of the image data to detect the one or more organs of the patient imaged in the displayed medical image of the patient comprises detecting and localizing one or more images of a corresponding one or more organs of the patient in the medical image; and
    the comparing of the medical report with the one or more organs imaged in the displayed medical image of the patient to detect one or more potential errors in the medical report comprises determining whether the one or more images of the corresponding one or more organs of the patient in the displayed medical image of the patient include an image of an organ of the patient referred to in the medical report.

7. A system of claim 6, wherein the non-transitory instructions are further executable by the one or more processors to cause the one or more processors to display a designation of an organ referred to in the medical report in the displayed medical image of the patient.

8. The system of claim 5, wherein the non-transitory instructions are further executable by the one or more processors to cause the one or more processors to:
    perform image processing of the image data to check for a potential pathology of an organ imaged in the displayed medical image of the patient; and
    output feedback indicative of a result of the check for the potential pathology of the organ imaged in the displayed medical image of the patient.

9. The system of claim 5, wherein the non-transitory instructions are further executable by the one or more processors to cause the one or more processors to determine whether an image of an organ referred to in the medical report is included in a list of organs of the patient that can be imaged by the medical imaging system.

10. The system of claim 5, wherein:
the non-transitory instructions are further executable by the one or more processors to cause the one or more processors to limit a selection of the medical report to a list of selectable medical reports; and
each of the selectable medical reports is directed to an organ of the patient for which an image of the organ is included in the displayed medical image of the patient.

11. The system of claim 5, wherein the non-transitory instructions are further executable by the one or more processors to cause the one or more processors to:
receive an input designating a portion of the displayed medical image of the patient; and
limit a selection of the medical report to a list of one or more selectable medical reports, wherein each of the one or more selectable medical reports corresponds to the designated portion of the displayed medical image of the patient.

12. The system of claim 5, wherein the medical imaging system comprises one or more of an X-ray imaging system, a computed tomography (CT) imaging system, a magnetic resonance imaging (MM) system, or an ultrasound imaging system.

13. A computer-implemented method of providing feedback identifying a potential error in a medical report, the method comprising:
receiving image data for a medical image of a patient by a medical report generation system, wherein the image data is generated via a medical imaging system;
displaying the medical image of the patient via one or more displays of the medical report generation system;
monitoring content of the medical report by the medical report generation system during preparation of the medical report;
processing the image data by the medical report generation system to detect one or more organs of the patient imaged in the displayed medical image of the patient;
comparing, by the medical report generation system, the content of the medical report with the one or more organs imaged in the displayed medical image of the patient to detect one or more potential errors in the medical report; and
outputting feedback by the medical report generation system indicative of the one or more potential errors in the medical report.

14. A computer-implemented method of claim 13, wherein:
the processing of the image data to detect the one or more organs of the patient imaged in the displayed medical image of the patient comprises detecting and localizing one or more images of a corresponding one or more organs of the patient in the displayed medical image of the patient; and
the comparing of the content of the medical report with the one or more organs imaged in the displayed medical image of the patient to detect one or more potential errors in the medical report comprises determining whether the one or more images of the corresponding one or more organs of the patient in the displayed medical image of the patient include an image of an organ of the patient referred to in the medical report.

15. A computer-implemented method of claim 14, comprising displaying, by the medical report generation system, a designation of an organ referred to in the medical report in the displayed medical image of the patient.

16. The computer-implemented method of claim 13, comprising:
performing image processing of the image data by the medical report generation system to perform a check for a potential pathology of an organ imaged in the displayed medical image of the patient; and
outputting feedback, by the medical report generation system, indicative of results of the check for a potential pathology of an organ imaged in the displayed medical image of the patient.

17. The computer-implemented method of claim 13, comprising determining, by the medical report generation system, whether an image of an organ referred to in the medical report is included in a list of organs of the patient that can be imaged by the medical imaging system.

18. The computer-implemented method of claim 13, comprising limiting a selection of the medical report, by the medical report generation system, to a list of selectable medical reports, wherein each of the selectable medical reports is directed to an organ of the patient for which an image of the organ is included in the displayed medical image of the patient.

19. The computer-implemented method of claim 13, comprising:
receiving, by the medical report generation system, an input designating a portion of the displayed medical image of the patient; and
limiting, by the medical report generation system, a selection of the medical report to a list of one or more selectable medical reports, wherein each of the one or more selectable medical reports corresponds to the designated portion of the displayed medical image of the patient.

20. The computer-implemented method of claim 13, wherein the medical imaging system comprises one or more of an X-ray imaging system, a computed tomography (CT) imaging system, a magnetic resonance imaging (MRI) system, or an ultrasound imaging system.

* * * * *